(12) United States Patent
Mankovich et al.

(10) Patent No.: US 9,348,813 B2
(45) Date of Patent: May 24, 2016

(54) TEXT ANALYSIS SYSTEM

(71) Applicant: KONINKLIJKE PHILIPS N.V., Eindhoven (NL)

(72) Inventors: Gabriel Ryan Mankovich, Yorktown Heights, NY (US); Richard Vdovjak, Eindhoven (NL); Anca Ioana Daniela Bucur, Eindhoven (NL); Yuechen Qian, Briarcliff Manor, NY (US); Merlijn Sevenster, New York, NY (US); Thusitha Dananjaya De Silva Mabotuwana, Yonkers, NY (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/368,938

(22) PCT Filed: Dec. 17, 2012

(86) PCT No.: PCT/IB2012/057384
§ 371 (c)(1),
(2) Date: Jun. 26, 2014

(87) PCT Pub. No.: WO2013/098701
PCT Pub. Date: Jul. 4, 2013

(65) Prior Publication Data
US 2014/0343925 A1 Nov. 20, 2014

Related U.S. Application Data

(60) Provisional application No. 61/580,334, filed on Dec. 27, 2011.

(51) Int. Cl.
*G06F 17/27* (2006.01)
*G06F 17/24* (2006.01)
*G06F 17/30* (2006.01)
*G06F 19/00* (2011.01)

(52) U.S. Cl.
CPC .......... *G06F 17/2785* (2013.01); *G06F 17/241* (2013.01); *G06F 17/30731* (2013.01); *G06F 19/322* (2013.01); *G06F 19/3487* (2013.01)

(58) Field of Classification Search
CPC ................... G06F 17/2785; G06F 17/30731
USPC ........................................................ 704/1–10
See application file for complete search history.

(56) References Cited

U.S. PATENT DOCUMENTS 7,493,253 B1 2/2009 Ceusters et al.
8,001,152 B1 * 8/2011 Solan .................. G06F 17/2785
707/791

(Continued)

FOREIGN PATENT DOCUMENTS

EP 1361522 A2 11/2003
EP 2182447 A1 5/2010

OTHER PUBLICATIONS

Corcho, O. et al. "Combination of DROOL rules and Protege knowledge bases in teh ONTO-H annotation tool", Workshop Protege with Rules, 8th Intl. Progege Conference. Jul. 18, 2005.

(Continued)

*Primary Examiner* — Marcellus Augustin

(57) ABSTRACT

A text analysis system is described. A natural language input unit (1) is arranged for enabling a user to input a free text (10) in a natural language. A natural language processing unit (2) is arranged for processing at least a portion of the free text (10) while it is being inputted, to obtain an explicit representation (11) of semantics represented by the free text. An explicit information input unit (3) is arranged for enabling the user to input explicit information (12) relating to the explicit representation (11) of semantics. The system comprises a visualization unit (4) for visualizing at least part of the explicit representation (11) to the user while the user is still inputting the free text (10). A user interface (5) is arranged for providing a user with simultaneous access to both the natural language input unit (1) and the explicit information input unit (3).

14 Claims, 4 Drawing Sheets

(56) References Cited

U.S. PATENT DOCUMENTS

| | | | |
|---|---|---|---|
| 8,442,940 B1* | 5/2013 | Faletti et al. | 707/610 |
| 2003/0158723 A1 | 8/2003 | Masuichi et al. | |
| 2006/0235881 A1 | 10/2006 | Masarie et al. | |
| 2009/0106047 A1* | 4/2009 | Bay | A61B 19/00 705/2 |
| 2010/0131923 A1* | 5/2010 | Oon | 717/108 |
| 2011/0033093 A1 | 2/2011 | Salz et al. | |
| 2014/0019128 A1* | 1/2014 | Riskin et al. | 704/235 |

OTHER PUBLICATIONS

Zheng, S. et al. "Bridging the unstructured and structured worlds: an adaptive self learning medical form generating system". MIXHS '12 Proceedings of the 2nd International Workshop. Oct. 29, 2012, pp. 59-66.

Modritscher, F. et al. "Utilizing Text Mining Techniques to Analyze Medical Diagnoses". International Conferences on New Media Technology and Semantic Systems, Graz, Austria, Sep. 5-7, 2007, p. 364-371.

Sahay, S. et al. "Semantic Annotation and Inference for Medical Knowledge Discovery". NSF Symposium on Next Generation of Data Mining, 2007, Baltimore, NSF Symposium Proceedings.

Chen, H. et al. "Knowledge Management, Data Mining, and Text Mining in Medical Informatics". Integrated Series in Information Systems, vol. 8, 2005.

* cited by examiner

TEXT ANALYSIS SYSTEM

This application is a national stage application under 35 U.S.C. §371 of International Application No. PCT/IB2012/057384 filed on Dec. 17, 2012 and published in the English language on Jul. 4, 2013 as International Publication No. WO/2013/098701, which claims priority to U.S. Application No. 61/580,334 filed on Dec. 27, 2011, the entire disclosures of which are incorporated herein by reference.

FIELD OF THE INVENTION

The invention relates to text analysis.

BACKGROUND OF THE INVENTION

Electronic health record (EHR) systems are currently being widely implemented to help manage patient records, increase the ability of analysts to assess quality of healthcare, and reduce patient suffering due to medical errors. Clinical decision support tools are essential components to leverage on the value of the data collected in EHR systems. Such tools may allow doctors to use the information/data to reach patient-specific decisions. While textual description in natural languages is one of the main modalities in EHR data, tools are yet to be developed to automatically, robustly, and accurately extract useful information from patient records.

A significant barrier to implementing such methods within the clinical setting is the lack of machine/computer understandable clinical text. By this it is meant that the meaning of text reports created in clinical practice normally cannot be extracted by a computer or other kind of machine. Clinical reports, such as discharge summaries, radiology and pathology reports, etc. are typically stored in natural language documents, rather than in more semantics-aware structured data formats. Such structured and semantically-rich data formats are useful when implementing more advanced supporting tools, such as clinical decision support (CDS) tools. To overcome this barrier, various natural language processing (NLP) and machine learning techniques have been developed specifically for identifying concepts and relationships in free text. However, much of the work in this field has been conducted using scientific textual data, which differs in important ways from the grammar-free, idiosyncratic text commonly found in clinical reports. The task of using NLP approaches to extract relevant information in real clinical cases has proven to be an extremely challenging one. While free text is here to stay, being the preferred way of reporting for clinicians, for both objective and subjective reasons, computers do not cope well with free text when it comes to interpreting the semantics. While the amounts of data collected within clinical care increase, it becomes increasingly harder for clinical users to make sense out of that data, and to filter and extract the pieces of information that are actually relevant. In this context, making the data understandable to the computer, including the semantics hidden in the data, becomes very valuable. For example, to find patients that are eligible for a particular clinical trial, the eligibility criteria of the trial need to be reliably compared with data in the patient record. The approach of fully structuring the data collected in clinical care has been received with a lot of resistance in the clinical domain. Additionally, recent studies deem such a fully structured approach as unrealistic and counterproductive, due to the complexity of clinical care and of the associated reporting.

U.S. Pat. No. 7,493,253 B1 discloses a system and a method for the indexing of free text documents using both language dependent terms and a language independent formal ontology of concepts to extract the deep meaning in free text documents. The natural language understanding system is taught what are and are not appropriate relationships between concepts by providing the linguistic ontology as part of the formal ontology. The linguistic ontology contains the rules about how language works as well as the principles that the human mind adheres to when representing reality at the conscious level of a human being.

US 20110033093 discloses a method of reporting of radiological information. A system and method are provided for the graphical presentation of the contents of radiological image study reports. Also, a system and method are provided for presenting the contents of structured radiological reports including multiple imaging studies and their corresponding findings in a single diagram. An ontology of radiological knowledge is used to interpret report content and generate information to be displayed in the graphical diagram.

SUMMARY OF THE INVENTION

It would be advantageous to have an improved analysis of free text, in particular to provide a computer with a deeper understanding of the free text. To better address this concern, a first aspect of the invention provides a text analysis system, comprising a natural language input unit for enabling a user to input a free text in a natural language;

a natural language processing unit for processing at least a portion of the text while it is being inputted, to obtain an explicit representation of semantics entailed by the free text; and an explicit information input unit for enabling the user to input explicit information relating to the explicit representation of semantics.

The described system provides an efficient way to produce an explicit representation of semantics expressed by free text generally created in reporting workflows. The explicit representation may be a structured representation, or particularly a machine-readable or machine-understandable representation. By performing the natural language processing as the free text is inputted by the user, while enabling the user to provide explicit information relating to the explicit representation of the semantics, in addition to the free text, valuable information is collected about the semantics that the author of the free text intends to express by the free text. Such information can be used in at least two ways: First, to improve the explicit representation of the semantics describing this particular free text, to better understand the semantics represented by the text. Second, to improve a natural language processing algorithm, to fine-tune parameters thereof, or to improve an ontology used in the natural language processing algorithm. The system may be arranged for continuously or regularly updating the explicit representation of semantics represented by the free text whenever additional text has been input by the user, or whenever the user has provided explicit information relating to the explicit representation of semantics.

The system may comprise a visualization unit for visualizing at least part of the explicit representation to the user while the user is still inputting the free text. This allows the user to review the generated explicit representation, and make corrections or additions to it as needed. Since the user is presented the representation while the user is still authoring the document, it is easier for the user to provide accurate corrections, because the user knows what he or she intends to express by the free text. For example, the visualization may be updated whenever a new portion of free text, such as a sentence, has been inputted.

The system may comprise a user interface arranged for providing a user with simultaneous access to both the natural language input unit and the explicit information input unit. This may be accomplished, for example, using graphical user interface elements, or widgets, that are displayed one beside the other, such that the user can select any one of them by causing a click event or a touch event. The user may thus be enabled to enter some free text using the natural language input unit, then input some explicit information using the explicit information input unit, and after that continue with inputting more free text. This way, the user can convey the desired information to the system using a combination of free text and explicit information and make any corrections to the explicit information directly when the user is inputting the free text. The user does not have to perform any retrospective review of the data to verify correctness.

The input unit may be arranged for enabling the user to confirm or reject the explicit representation of semantics. This allows the system to propose an alternative explicit representation, in response to a rejection. Alternatively, the system may collect the confirmations/rejections and use it as information to make improvements to the natural language processing system, as discussed above.

The input unit may be arranged for enabling the user to input information relating to a correction of an error in the explicit representation of the semantics. This information may be used to improve the representation, or to collect ground truth pairs of free text and corresponding explicit semantic structure.

The input unit may be arranged for enabling the user to provide information relating to an addition, a change, or a deletion of an instance of a concept or a semantic relation between two instances of concepts. These are examples of information pieces that contain relevant information to include in the explicit representation of the semantics.

The system may comprise an associating unit for creating an association between a portion of the text and a corresponding portion of the explicit representation of semantics, wherein the corresponding portion of the explicit representation of semantics represents the semantics of the portion of the text. This allows to perform a check on the correctness and allows to reconstruct where a portion of the explicit representation was derived from. Moreover, when corrections have been made to the corresponding portion of the explicit representation, it allows to trace what portion of the free text could not be processed automatically. This information helps to improve the natural language processing system.

The associating unit may be arranged for creating the association based on the explicit information inputted by the user. The input by the user may provide clues to the portion of the free text that the input relates to. For example, when the user notes an error in the explicit representation, and corrects it, there is a clue that the correction relates to the portion of text just typed. Alternatively, the system may be arranged for enabling the user to explicitly indicate a portion of the free text, for example by highlighting, and indicate that a correction, or a particular portion of the explicit semantics, corresponds to the highlighted free text portion. This provides more detailed ground truth information of the relationship between the free text and the explicit information.

The system may comprise an updating unit for generating an updated explicit representation of semantics represented by the text, based on the explicit information inputted by the user. This updating unit uses the input provided by the user to produce the improved updated explicit representation of semantics.

The system may comprise a storage unit for storing the free text and at least two of: the explicit information inputted by the user, the explicit representation of semantics generated by the natural language processing unit, and the updated explicit representation of semantics represented by the text. This allows to review the corrections for each case, together with the free text. It provides information as to how the natural language processing system may be improved.

The system may comprise a reward generator for generating an indication of a reward for the user, based on the explicit information relating to the explicit representation of semantics inputted by the user. This provides an incentive for the user to provide the feedback when using the system. For example, a physician may be motivated by the reward to provide feedback on the explicit representation of the semantics during his or her regular work of entering reports. This way, valuable information may be collected that is of interest when improving the natural language processing system.

The system may comprise an algorithm improvement unit for improving a natural language processing algorithm that is used by the natural language processing unit, based on the explicit information inputted by the user. This allows to automatically improve the algorithm used for natural language processing, so that in the future fewer corrections may be needed.

In another aspect, the invention provides a workstation comprising the system set forth.

In another aspect, the invention provides a healthcare information system for providing an electronic reporting workflow. The healthcare information system may comprise the system set forth. The healthcare information system may further comprise an electronic health record database for storing the free text reports. This integration of the system in a healthcare information system allows the feedback collection to be implemented as an integral part of the healthcare workflow. This way, feedback collection may be more efficient, and/or the collected feedback may be more complete.

In another aspect, the invention provides a text analysis method, comprising enabling a user to input a free text in a natural language;

processing at least a portion of the free text using natural language processing while it is being inputted, to obtain an explicit representation of semantics represented by the free text; and enabling the user to input explicit information relating to the explicit representation of semantics.

In another aspect, the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the workstation, the healthcare information system, the text analysis system, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated hereinafter with reference to the drawings.

DETAILED DESCRIPTION OF EMBODIMENTS

Figure 1:
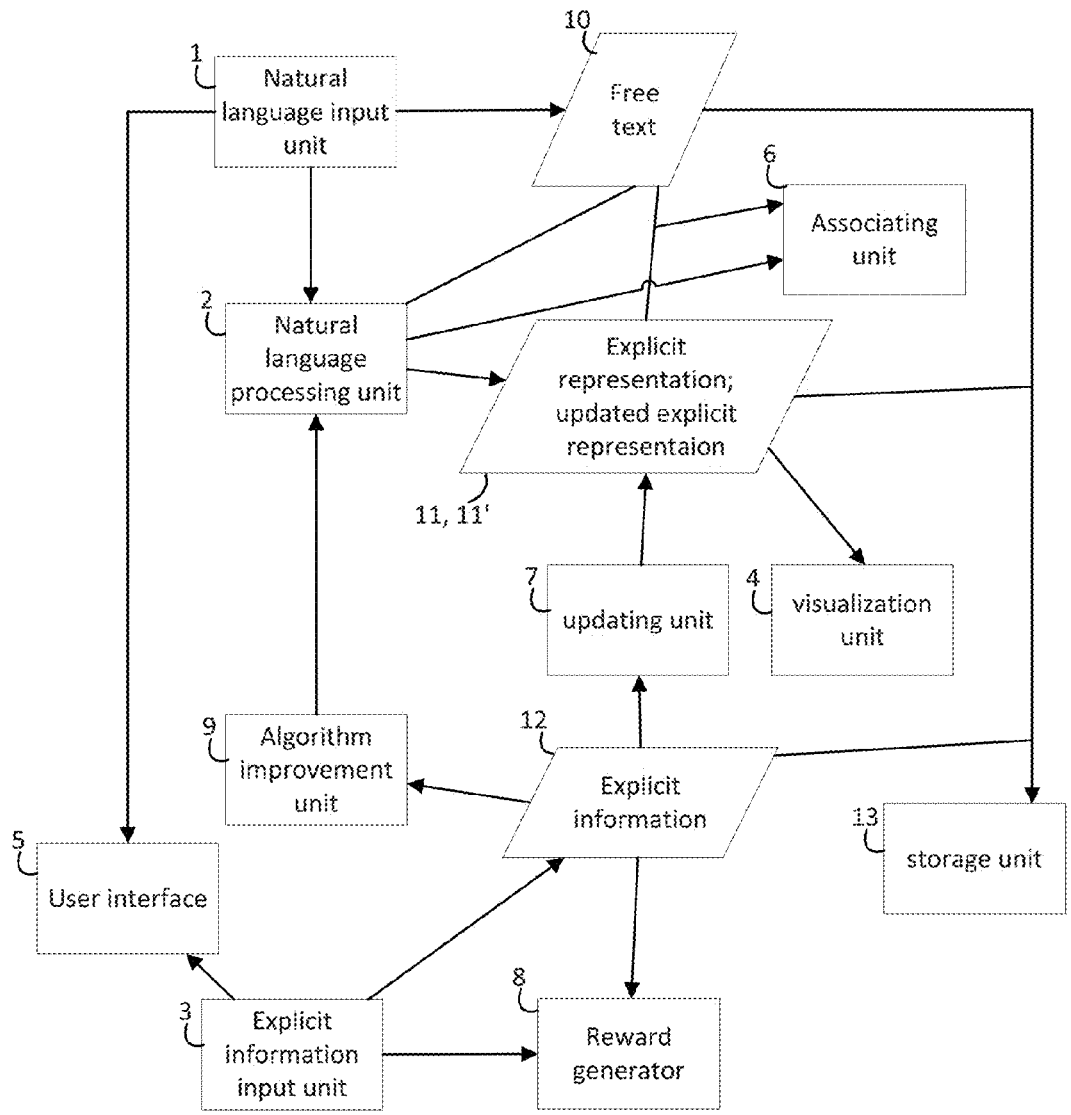
FIG. 1 is a block diagram showing aspects of a text analysis system.

FIG. 1 shows schematically components of a text analysis system. The text analysis system may be implemented on a workstation or as part of a distributed computing environment, such as a healthcare information system, for example. The system may also be implemented using dedicated electronic circuitry. The system may comprise user interface hardware, such as a display, touch screen, keyboard, pointing device, and the like, for allowing a user to operate the system and provide the user inputs described herein. A microphone, in conjunction with speech recognition software or hardware, may also be part of the system. The system may comprise, or be operatively connected to, a data storage system, such as a database system, more particularly a health record database system or a hospital information system, or a file system, to store documents such as the created free text documents and/or structured documents representing the semantics of the free text documents in an explicit format.

The system may also be implemented as a plug-in of a document creation system, such as a radiology reporting system or a healthcare information system, such as an electronic health record system. This way, the reporting features of the existing system may be extended with on-the-fly natural language processing to extract an explicit representation 11 of the semantics of the free text 10 report, and on-the-fly collection of user-provided explicit semantic information 12 relating to the explicit representation 11 of the semantics of the report that is being created.

The system may comprise a natural language input unit 1 arranged for enabling a user to input a free text 10 in a natural language. This natural language input unit 1 may comprise a conventional text editor or a dictation system with real-time speech recognition. However, the natural language input unit 1 is arranged for forwarding any free text to the natural language processing unit, as soon as it is received.

The natural language input unit 1 may also comprise a software interface to a healthcare information system. For example, the system can be a plug-in of the healthcare information system. The plug-in can communicate with the healthcare information system. The healthcare information system may be arranged for regularly feeding the natural language input unit 1 with any free text inputted by the user via the healthcare information system's reporting subsystem. Such a natural language input unit 1 may also be connected to a radiology viewing station; for example, when an image is viewed, automatically a text entry window may pop up, enabling the physician to provide comments to the image.

The system may comprise a natural language processing unit 2 arranged for processing at least a portion of the free text 10 while it is being inputted. Consequently, the processing is started using incomplete text information, based on the portion of free text that has been entered up to now. The natural language processing may result in an explicit representation 11 of semantics represented by the free text. Natural language processing techniques are known in the art per se. Consequently, these are not described in detail herein. However, it is possible to apply techniques such as template matching, and identification of instances of concepts, that are defined in ontologies, and relations between the instances of the concepts, to build a network of instances of semantic concepts and their relationships, as expressed by the free text. This explicit semantic information may be expressed in a computer-readable format, such as the XML format. Such a computer-readable format may be compliant with a machine-understandable format such as Resource Description Framework (RDF), Resource Description Framework Schema (RDFS), Web Ontology Language (OWL).

The system may comprise an explicit information input unit 3 arranged for enabling the user to input explicit information 12 relating to the explicit representation 11 of semantics. This explicit information 12 may comprise an indication of an explicit semantic concept or a semantic relationship that is expressed by the free text. Such an explicit information input unit 3 may be implemented in many different ways. For example, it is possible to enable the user to input a snippet of XML code that contains semantic information, as described above. Alternatively, various graphical user interface elements may be implemented that allow input of explicit semantic information. For example, a list of most-likely-intended concepts and/or relationships may be presented, from which the user may be enabled to make a selection. This allows the system to resolve ambiguities in the free text by asking the user to make a selection from the possible different interpretations of the free text. Other possibilities will be described hereinafter.

The system may comprise a visualization unit 4 for visualizing at least part of the explicit representation 11 to the user while the user is still inputting the free text 10. Such a visualization can take the form of displaying a 'raw version' of the explicit representation 11. In case the raw version comprises XML, for example, an XML viewer may be used. Alternatively, a graphical visualization is generated. Such a graphical visualization can be made in different ways. For example, instances of concepts that are used in the free text can be made the nodes of a graph, and the term identifying the concept can be shown in a symbol representing the node. Edges between the nodes can be used to denote the relations between the instances of the concepts. The edges can be annotated with an indication of the kind of relationship between two connected instances of concepts.

The system may comprise a user interface 5 arranged for providing a user with simultaneous access to both the natural language input unit 1 and the explicit information input unit 3. For example, two windows may be shown on a display device, one window for inputting free text 10, and the other for inputting explicit information 12. The window for inputting the free text 10 may comprise a text editor, for example. The window for inputting explicit information 12 may show the visualization of the explicit representation 11 of semantics. The user may be enabled to interact with the latter visualization to make changes, or additions, as a way to input the explicit information 12. For example, the graphical representation using a graph with nodes and edges can be made interactive such that the edges can be dragged and dropped and/or terms shown in the nodes can be replaced with more appropriate terms, and other kinds of interactivity may be provided.

The explicit information input unit 3 may be arranged for enabling the user to confirm or reject the explicit representation 11 of the semantics. This may be implemented using a simple radio button or check button, and stored as a Boolean variable as explicit information 12.

The explicit information input unit 3 may be arranged for enabling the user to input information relating to a correction in the explicit representation 11 of the semantics. This may be implemented, as mentioned above, using a drag/drop and other interactivity of a visualization of the explicit representation 11. Alternatively, the system may provide a command prompt enabling the user to enter the corrections as commands, optionally using speech recognition techniques.

The explicit information input unit 3 may be arranged for enabling the user to provide information relating to an addition, a change, or a deletion of an instance of a concept or a semantic relation between two instances of concepts. Again, this can be implemented using drag and drop functionality or in another way, as described above or otherwise.

The system may comprise an associating unit 6 for creating an association between a portion of the free text 10 and a corresponding portion of the explicit representation 11 of semantics. The associating unit 6 may be operatively connected to the natural language processing unit 2, to receive information about which semantic elements are extracted from which portion of the free text. The corresponding portion of the explicit representation 11 of semantics should represent the semantics of the portion of the free text 10 with which it is associated. These associations can be stored, for example, within the data structure storing the explicit representation 11 of semantics. The associations can also be stored as a separate data structure.

The associating unit may also be arranged for creating the association based (also) on the explicit information inputted by the user. For example, the user may be enabled to provide an explicit indication of the text portion to which a particular semantic construct relates.

The system may comprise an updating unit 7 for generating an updated explicit representation 11' of semantics represented by the free text 10, based on the explicit information 12 inputted by the user. This is an optional feature of the system, because one application of the system may be to collect the explicit information 12 as feedback to be able to make future improvements to the system. The updating unit 7 may be integrated with the explicit information input unit, in particular when the explicit information is provided by the user as edits of the explicit representation 11,11' of semantics.

The system may comprise a storage unit 13. Such a storing unit may be arranged for logging any edits made by the user to the explicit representation 11,11' via the explicit information input unit 3. This way, the explicit information 12 may be preserved for future use. Such future use may comprise improving the natural language processing, for example by employing machine learning. In addition, or alternatively, the storage unit 13 may be arranged for storing the explicit representation 11 of semantics generated by the natural language processing unit, and/or the updated explicit representation 11' of semantics represented by the text. At least two of: the explicit information 12, the explicit representation 11, and the updated explicit representation 11' may allow to identify which aspects of the explicit representation 11 needed correction by the user. This allows to identify and improve upon weak points of the natural language processing algorithm that is used. Storing the free text 10 also allows to match the explicit representation against the explicit representations 11,11' and/or the explicit information 12, in particular corrections made by the user to the explicit representation 11.

The system may comprise a reward generator 8 arranged for generating an indication of a reward for the user, based on the explicit information 12 relating to the explicit representation 11 of semantics inputted by the user. This reward may be given to the user either automatically or by intervention of a human controller. For example, a financial reward may be given to the user when the user has provided a substantial amount of explicit information 12 to improve the semantics. This may help to motivate the user to provide relevant feedback.

The system may comprise an algorithm improvement unit 9 arranged for improving a natural language processing algorithm that is used by the natural language processing unit 2, based on the explicit information 12 inputted by the user. This may be performed by a machine learning algorithm. The algorithm improvement unit 9 may comprise a user interface for enabling a human operator to control the improvements actually applied to the machine learning algorithm. Aspects of the machine learning algorithm that may be subject to improvement in this way include: an ontology, a parameter of the natural language processing algorithm, or algorithmic steps of the natural language processing algorithm.

Figure 2:
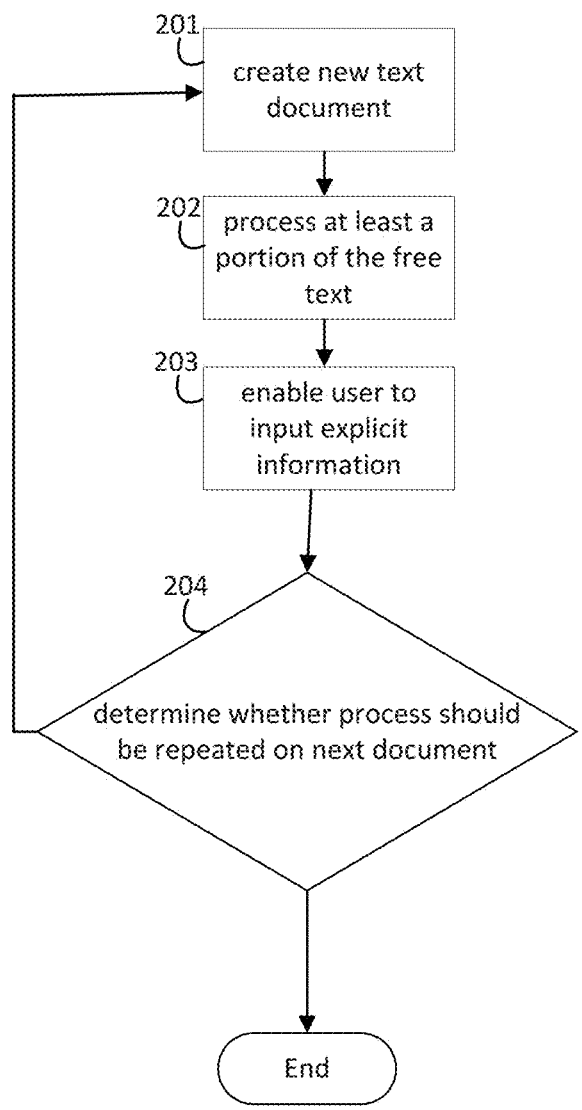
FIG. 2 is a flowchart showing aspects of a text analysis method.

FIG. 2 shows a flowchart of an example implementation of a text analysis method. The method may start with step 201 of enabling a user to input a free text in a natural language. While the user is inputting portions of the free text, the method may perform step 202 of processing at least a portion of the free text, insofar as it has been inputted, using natural language processing techniques, for example according to a predetermined natural language processing algorithm. This may result in an explicit representation of semantics entailed by the free text, insofar the free text has been inputted already. While the user is inputting portions of the free text, the method may perform the step 203 of enabling the user to input explicit information relating to the explicit representation of semantics. The user may, for example, be enabled to provide such explicit information at any time during the input of the free text. After performing these steps, it may be determined in step 204 whether the process should be repeated on a next document. If so, the method starts again from step 201 to create a next document with free text and corresponding explicit representation of semantics.

The method may be extended or modified based on the description of the functionality of the system herein. Likewise, the system may be extended or modified based on the description of the method. The method may be implemented using software and/or using dedicated hardware.

Homonymy, polysemy, co-reference, direct and implied negation, temporality are linguistic features often to be found in clinical reports which are notoriously difficult for NLP frameworks to address and to extract the intended meaning. Due to the ambiguity of the natural language, in some cases even a human expert does not extract the original meaning of the text description as intended by the author.

To provide future intelligent clinical decision support systems (CDS) with structured, semantically sound and well-described data that allows a CDS to perform automated reasoning, the data capture of today may need to be improved. Retrospective analysis of existing text reports and trying to guess the hidden meaning may not be efficient.

In theory, imposing rigorous structured reporting for all data capture and disallowing free text fields would produce much more structured and computer-processable data, but it is unrealistic to assume that this would be accepted by the clinicians. Moreover, it is unrealistic to believe that structured reports will be able to capture all the complexity and the necessary nuances of free text reporting. So while the information would become easier to process by computer, some of the necessary meaning may be lost. The ease of use and the expressivity of free text is something that clinicians may demand in most of their reporting systems for many years to come. Of course some partial structured reporting solutions are being successfully used in a number of medical subdomains e.g. the BI-RADS reporting standard in breast cancer, there is however still the need to have the free text accompanying the report.

Most existing NLP systems that attempt to extract the semantics from free text offer very little, if any, verification that the extracted meaning is really what was actually intended by the author. Such verification is hard or even impossible if we deal with historical data, inter alia because the author of historical data may not be available anymore.

Many difficulties described above stem from the fact that the system (or a human expert) needs to "second-guess" the intended semantics. Provided in this description is a system which would enable the creator of the data to check and provide a feedback on the intended semantics if necessary, all this on-the-fly at the time of data entry.

One of the reasons for this is that the author knows best the meaning of the text he or she is writing, and verifying this right at data entry makes later second guessing unnecessary. This approach also allows for the system to learn and personalize the NLP pipeline e.g. with preferred phrases the user chooses in his or her descriptions.

The semantics of a free-text narrative may be captured by a semantic graph.

The techniques disclosed herein may be used to record the user's feedback and learn from it making the natural language processing system more personalized, tailoring it to particular nuances of the clinical domain and the "writing style"/phrasing of the user.

Figure 3:
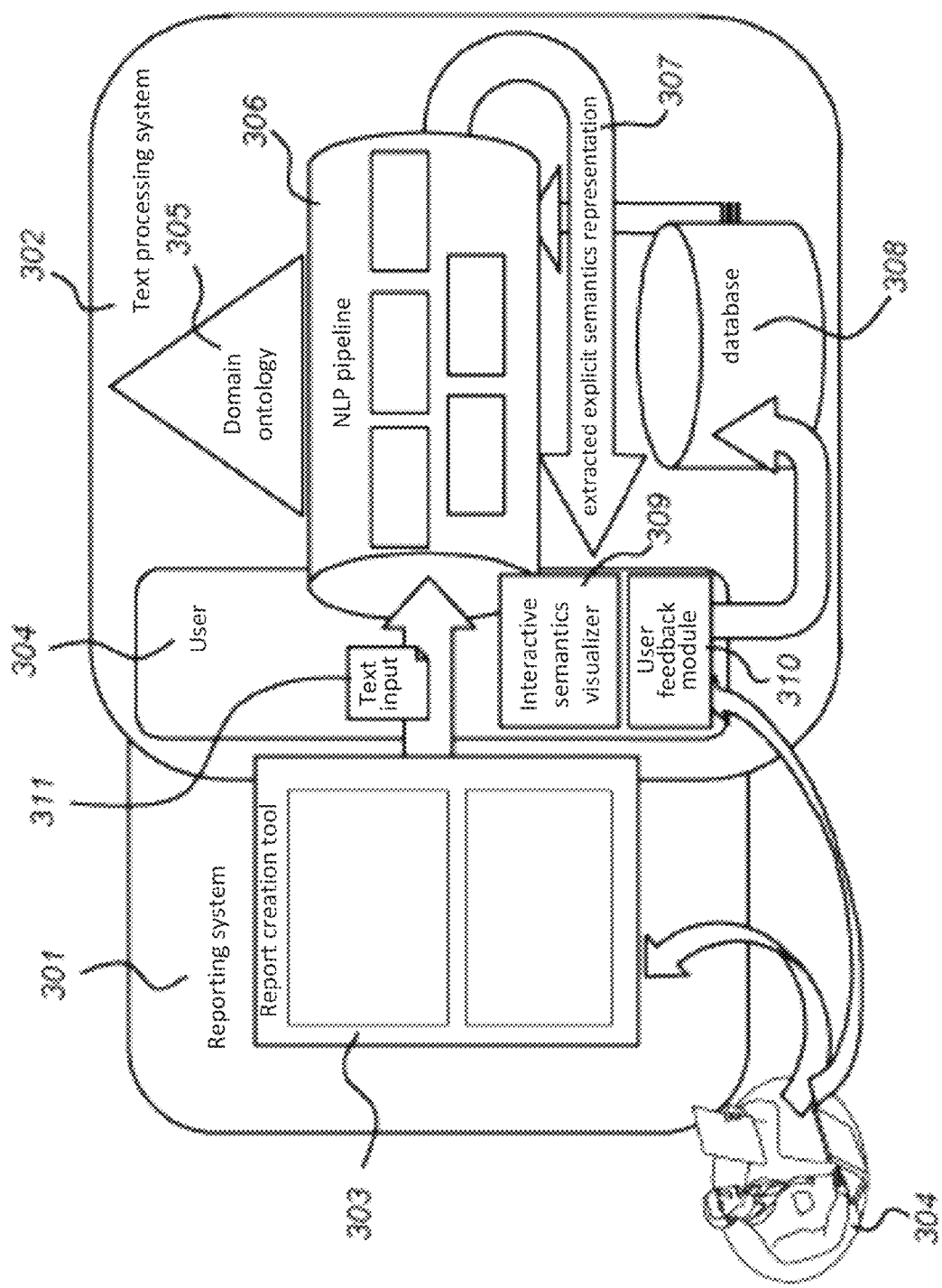
FIG. 3 is another block diagram showing aspects of a text analysis system.

FIG. 3 illustrates a diagrammatic view of an integrated document creation and processing system. The system comprises a reporting system 301 and a text processing system 302. The reporting system 301 may be part of an existing healthcare information system, and the text processing system 302 may be implemented as a plug-in or extension of the existing reporting system 301. Alternatively, the two systems are implemented as an integral unit. The reporting system 301 comprises a report creation tool 303 that allows the user 304, for example a clinician, to create a text document or report. The report, as it is being created, is provided as an on-the-fly text input 311 to a natural language processing plug-in 304 of the text processing system 302. The text input 311 is fed to an NLP pipeline 306 that performs on-the-fly extraction of semantic relationships from the text input 311, using the knowledge from a domain ontology 305 and a database 308 comprising e.g. personalized phrase patterns, ground truth, etc. The extracted explicit representation of semantics 307 is fed to an interactive semantics visualizer 309 (corresponding to visualization unit 4), that shows the extracted semantics to the user. A user feedback module 310 (corresponding to explicit information input unit 3) is arranged for collecting feedback on the visualized semantics from the user 304.

From the narrative free text as it is created by the user, a semantic graph is built by extracting the relevant set of concepts present in the narrative and building the relations among them and identifying the instances. The constructed graph of instances and their relations is presented to the user by the interactive semantics visualizer 309 to confirm or correct.

A distinction may be made between the schema level and the instance level. Known approaches to concept extraction focus only on schema level, which may stay too general for many clinical applications. At the instance level, instances of concepts are identified in the free text, as well as the literal values associated with the instances, when possible. These items are then presented to the user for review.

For example, when creating a report about a fracture of a patient's hip it is possible to describe and extract the laterality of it and the date when the fraction happened if available in the text. That would not be possible when only the level of concepts/schema is used.

Trying to capture a patient EHR record in a semantic graph may offer more flexibility compared to other representations (e.g. tables), as a directed labeled graph fits very well the underlying semantic relationships in a medical narrative which are often intertwined and cross-linked.

An example case will be described hereinafter. This example may be representative of cases frequently found in clinical reports. The semantic graph of the summary of a patient's medical history and of the family history may be extracted. The medical history may be important as it provides information for the current episode of care, it gives relevant context for both diagnosis and treatment. The family history may be relevant in various diseases that may have genetic origin (e.g. cancer, cardio-vascular), as it may suggest predisposition and increased risk in the current patient. The family history as well may be used for both diagnosis and treatment selection.

The system may be implemented, for example, by means of one or more of the following components interacting with each other.

A plug-in component 304 may be responsible for connecting with reporting software of the clinician. The application programming interface (API) of such plug-in can range from a simple text extraction module to full UI integration with the reporting system including the look and feel.

The plug-in 304 may provide user interface components that the user will see. First, the visualizer of the semantics this may be domain specific, covering the most important data items within the given clinical domain that the underlying NLP framework focuses to determine. For instance, in case of breast cancer, the visualizer could be implemented as graphical demonstration of where the tumor is located, indicating its size etc. Second, the feedback system may offer the user to provide feedback on the visualized extracted semantics. This component can range from simple yes/no (approve/disapprove) feedback options to more sophisticated UI enabling user-computer interaction such as entering structured data on request, in case the NLP framework made an error in determining them automatically.

The underlying system may also include a knowledge component describing a given clinical domain. This can be implemented for instance by an ontology extracted from SNOMED and tailored by domain experts if necessary. Such ontology should contain those semantic concepts that are of importance in the given clinical domain and hence the NLP framework should focus on determining their values/bindings.

An instance of an NLP pipeline 306 may be provided to perform semantics extraction. An NLP framework to extract explicit semantics from natural language may be implemented. This framework may contain components such as sentence detection, tokenizer, stemmer, negation detection etc.

A database 308 may be filled with the received user feedback. Each time the user interacts with the feedback module, the information may be stored in the database. This may contain the user confirmation of certain values in a given phrase. In time this information represents the user phrase choices and the intended meaning with respect to the ontology domain, which enables a true personalization of an NLP solution to a particular user.

An example of an excerpt from a free text is the following, hereinafter referred to as Example 1: "I have been asked to perform a medical oncology consultation on this patient for breast cancer. Ms. [name] is a [age] year old white female with multiple medical problems as outlined in the past medical history. She has lost some weight, but she does not know how much. Past medical history: She had an aortic aneurysm repair in the past. She also had a non-pathologic fracture of the left hip with a fall many years ago."

As one of the possible syntaxes for the semantic graph it is possible to use Resource Description Framework (RDF) and/or Resource Description Framework Schema (RDFS), as a standard provided by the W3C consortium. It is possible to use any existing tools and reasoners to process graphs adhering to that syntax.

An aspect of the NLP pipeline as proposed herein is that it may derive instances or occurrences of known classes or concepts, and the relationships between instances of these concepts. The known classes may be taken out of existing ontologies such as SNOMED. Those instances may be linked to literal values whenever possible, e.g. from the phrase "fracture of hip occurs laterally on the left", the instance of the concept "fracture of the hip" may be associated with the positional value "laterally on the left".

Figure 4:
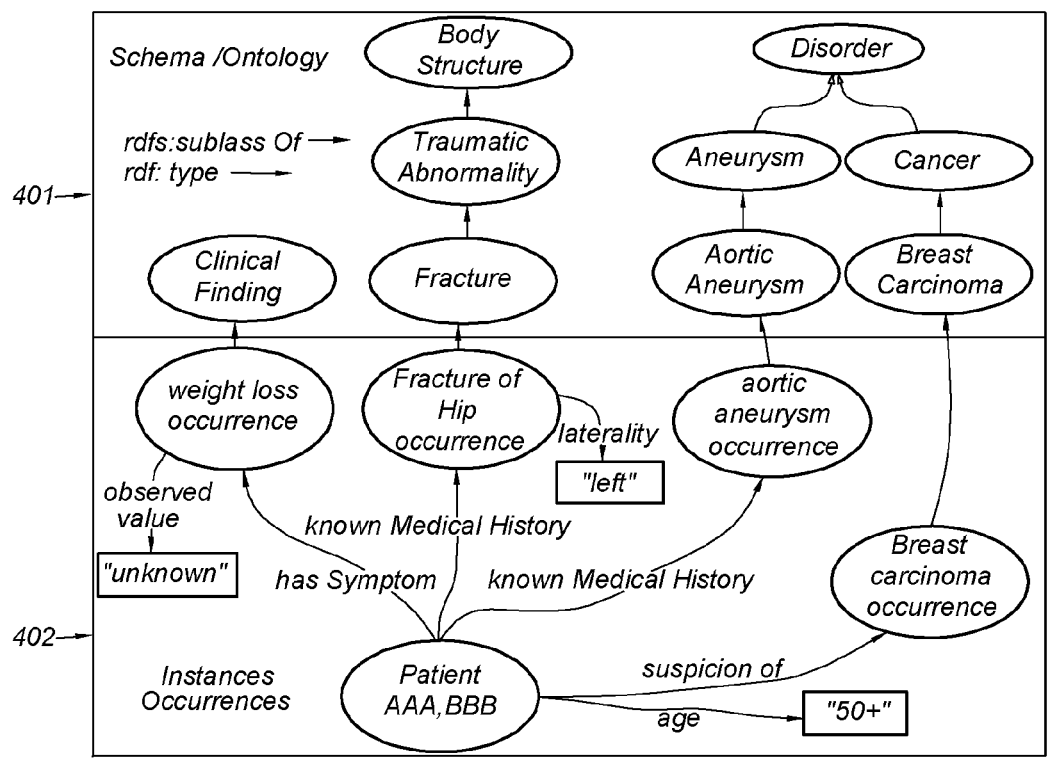
FIG. 4 illustrates a simplified ontology and a semantic graph.

The top half of FIG. 4 shows an excerpt of a hierarchy of classes 401 extracted from SNOMED. The bottom half of the Figure shows the semantic graph 402 of instances of the classes, that is, an explicit representation of the semantics of the sentences of Example 1 recited hereinabove.

When processing the text, such as the text of Example 1, several phases may be identified, in an example embodiment. However, these are only examples. Other implementations are also possible.

Phase 1: Identify the sections of interest. Based on a set of rules that can be customized for each institution, the relevant part of the report is selected. In this case, next to the section that specifically refers to the medical history, the system also selects the description of the present consultation as that contains relevant concepts for building the medical history of the current medical encounter.

Phase 2: Identify the relevant concepts referred to in the free text and the instances of these concepts. This step may be executed by means of the NLP. Components for sentence and word segmentation, part-of-speech tagging, stemming, negation detection, and more, may be used. The NLP pipeline may use the ontology to identify relevant concepts and their instances. Instances of classes may have relations among each other or properties with literal values. For example, hip fracture has a property laterality which in the case of Example 1 binds to a value left. Next to the relations from the ontology there may be a pre-defined set of relations that the system searches for.

Phase 3: Build the semantic graph for patient history. After identifying the relevant concepts and their relations, the system constructs a semantic graph using, for example, the RDF and/or RDFS syntax.

The system may be arranged for detecting an ambiguity in the free text. In this case, the user may be alerted by means of a visual indication, a sound signal, or another indication. The user may be presented with one or more proposals of explicit representation of semantics that is compatible with the free text, and the user may be enabled to make a selection and/or refine the free text to make the free text non-ambiguous.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A text analysis system comprising:
  a natural language input unit for enabling a user to input a free text in a natural language;
  a natural language processing unit for processing at least a portion of the free text while it is being inputted, to obtain an explicit representation of semantics entailed by the free text;

an explicit information input unit for enabling the user to input explicit information relating to the explicit representation of semantics; and a user interface for providing a user with simultaneous access to both the natural language input unit and the explicit information input unit;

wherein the explicit information input unit is arranged for enabling the user to confirm or reject the explicit representation of the semantics; and wherein the user interface is arranged for providing the user with an alternative explicit representation upon receipt of a rejection of the explicit representation of the semantics.

2. The system according to claim 1, comprising a visualization unit for visualizing at least part of the explicit representation to the user while the user is still inputting the free text.

3. The system according to claim 1, wherein the explicit information input unit is arranged for enabling the user to input information relating to a correction in the explicit representation of the semantics.

4. The system according to claim 1, wherein the explicit information input unit) is arranged for enabling the user to provide information relating to an addition, a change, or a deletion of an instance of a concept or a semantic relation between two instances of concepts.

5. The system according to claim 1, comprising an associating unit for creating an association between a portion of the free text and a corresponding portion of the explicit representation of semantics, wherein the corresponding portion of the explicit representation of semantics represents the semantics of the portion of the free text.

6. The system according to claim 1, comprising an updating unit for generating an updated explicit representation of semantics represented by the free text, based on the explicit information inputted by the user.

7. The system according to claim 1, comprising a storage unit for storing the free text in the natural language and at least two of: the explicit information inputted by the user, the explicit representation of semantics generated by the natural language processing unit, and the updated explicit representation of semantics represented by the text.

8. The system according to claim 1, further comprising a reward generator for generating an indication of a financial reward for the user, based on the explicit information relating to the explicit representation of semantics inputted by the user.

9. The system according to claim 1, comprising an algorithm improvement unit for improving a natural language processing algorithm that is used by the natural language processing unit, based on the explicit information inputted by the user.

10. A workstation comprising the system according to claim 1.

11. A healthcare information system for providing an electronic reporting workflow, comprising the system according to claim and an electronic health record database for storing the free text reports.

12. A text analysis method comprising:
enabling a user to input a free text in a natural language;
processing at least a portion of the free text using natural language processing while it is being inputted, to obtain an explicit representation of semantics entailed by the free text;
enabling the user to input explicit information relating to the explicit representation of semantics; and
wherein the user is provided with simultaneous access to both input a free text in a natural language and input explicit information relating to the explicit representation of semantics;
wherein the user is provided with options to confirm or reject the explicit representation of the semantics; and
wherein upon receipt of a rejection of the explicit representation of the semantics the user is provided with an alternative explicit representation.

13. A non-transitory computer readable storage medium comprising instructions for causing a processor system to perform the method according to claim 12.

14. A text analysis system comprising:
a natural language inputter configured to enable a user to input a free text in a natural language;
a natural language processor configured to process at least a portion of the free text while it is being inputted, to obtain an explicit representation of semantics entailed by the free text;
an explicit information inputter configured to enable the user to input explicit information relating to the explicit representation of semantics;
a user interface configured to provide a user with simultaneous access to both the natural language input unit and the explicit information input unit; and
a reward generator configured to generate an indication of a financial reward for the user, based on the explicit information relating to the explicit representation of semantics inputted by the user.

* * * * *